(12) United States Patent
Chew et al.

(10) Patent No.: US 12,213,918 B2
(45) Date of Patent: *Feb. 4, 2025

(54) CONTACT PROBE FOR THE DELIVERY OF LASER ENERGY

(71) Applicants: IRIDEX Corporation, Mountain View, CA (US); National University Hospital (Singapore) PTE LTD, Singapore (SG); National University of Singapore, Singapore (SG)

(72) Inventors: Paul T. K. Chew, Singapore (SG); David M. Buzawa, San Jose, CA (US); Giorgio Dorin, Cupertino, CA (US)

(73) Assignee: Iridex Corporation, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/197,956

(22) Filed: May 16, 2023

(65) Prior Publication Data

US 2023/0293351 A1    Sep. 21, 2023

Related U.S. Application Data

(63) Continuation of application No. 17/465,405, filed on Sep. 2, 2021, now Pat. No. 11,690,761, which is a
(Continued)

(51) Int. Cl.
*A61F 9/009* (2006.01)
*A61F 9/007* (2006.01)
*A61F 9/008* (2006.01)

(52) U.S. Cl.
CPC .............. *A61F 9/009* (2013.01); *A61F 9/008* (2013.01); *A61F 9/00781* (2013.01); *A61F 2009/00868* (2013.01); *A61F 2009/00891* (2013.01)

(58) Field of Classification Search
CPC ...... A61F 9/009; A61F 9/008; A61F 9/00781; A61F 2009/00868; A61F 2009/00891; A61F 9/00821
See application file for complete search history.

(56) References Cited

U.S. PATENT DOCUMENTS

| 2,033,397 A | 3/1936 | Frances |
| 5,151,098 A | 9/1992 | Loertscher |

(Continued)

FOREIGN PATENT DOCUMENTS

| CN | 107072712 A | 8/2017 |
| EP | 3160379 | 5/2017 |

(Continued)

OTHER PUBLICATIONS

"G-Probe™ Operator Manual", Iridex, 131 05-EN Rev D, May 2013, 17 pages.
(Continued)

*Primary Examiner* — Sarah W Aleman
*Assistant Examiner* — Mikail A Mannan
(74) *Attorney, Agent, or Firm* — Kilpatrick Townsend & Stockton LLP

(57) ABSTRACT

Systems, devices, and methods for treating a glaucomatous eye are provided. An amount of pulsed laser energy is delivered to the pars plana of the eye by a hand-holdable device which comprises a hand-holdable elongate member and a contact member disposed on an end of the elongate member. A contact surface of the contact member is placed in direct contact with the eye so that a reference edge of the contact member aligns with the limbus and a treatment axis defined by the elongate member is angularly offset from the optical axis of the eye. The amount of pulsed laser energy delivered is insufficient to effect therapeutic photocoagulation but is sufficient to increase uveoscleral outflow so as to
(Continued)

maintain a reduction from pre-laser treatment intraocular pressure. Amounts of pulsed laser energy will be transmitted to a circumferential series of tissue regions of the eye.

33 Claims, 9 Drawing Sheets

Related U.S. Application Data continuation of application No. 16/369,477, filed on Mar. 29, 2019, now Pat. No. 11,116,666, which is a continuation of application No. 14/579,783, filed on Dec. 22, 2014, now Pat. No. 10,292,868, which is a continuation of application No. 12/261,889, filed on Oct. 30, 2008, now Pat. No. 8,945,103.

(60) Provisional application No. 60/983,811, filed on Oct. 30, 2007.

(56) References Cited

U.S. PATENT DOCUMENTS

| | | | |
|---|---|---|---|
| 5,174,304 | A | 12/1992 | Latina et al. |
| 5,217,452 | A | 6/1993 | O'donnell |
| 5,372,595 | A | 12/1994 | Gaasterland et al. |
| 5,514,125 | A | 5/1996 | Lasser et al. |
| 5,549,596 | A | 8/1996 | Latina |
| 5,549,632 | A | 8/1996 | Lai |
| 5,968,033 | A | 10/1999 | Fuller et al. |
| 6,059,772 | A | 5/2000 | Hsia et al. |
| 6,454,763 | B1 | 9/2002 | Motter et al. |
| 8,588,268 | B2 | 11/2013 | Boutoussov et al. |
| 8,945,103 | B2 | 2/2015 | Chew et al. |
| 9,700,461 | B2 | 7/2017 | Buzawa et al. |
| 9,820,883 | B2 | 11/2017 | Berlin |
| 9,835,795 | B2 | 12/2017 | Thomsen et al. |
| 10,292,868 | B2 | 5/2019 | Chew et al. |
| 10,369,049 | B1 | 8/2019 | Chen et al. |
| 10,500,094 | B2 | 12/2019 | Buzawa et al. |
| 11,116,666 | B2 | 9/2021 | Chew et al. |
| 11,690,761 | B2 | 7/2023 | Chew et al. |
| 2003/0109907 | A1 | 6/2003 | Shadduck |
| 2006/0021623 | A1 | 2/2006 | Miller et al. |
| 2006/0187978 | A1 | 8/2006 | Telfair et al. |
| 2010/0076419 | A1 | 3/2010 | Chew et al. |
| 2014/0121653 | A1 | 5/2014 | Abe et al. |
| 2015/0209179 | A1 | 7/2015 | Chew et al. |
| 2015/0305938 | A1 | 10/2015 | Vold et al. |
| 2015/0374539 | A1 | 12/2015 | Buzawa et al. |
| 2016/0074672 | A1 | 3/2016 | Schomacker et al. |
| 2017/0000648 | A1 | 1/2017 | Chabrier et al. |
| 2018/0000638 | A1 | 1/2018 | Buzawa et al. |
| 2020/0306080 | A1 | 10/2020 | Herekar et al. |

FOREIGN PATENT DOCUMENTS

| | | |
|---|---|---|
| EP | 3160379 B1 | 6/2019 |
| HK | 1232094 | 1/2018 |
| JP | 07250862 A | 10/1995 |
| JP | 2002282298 A | 10/2002 |
| SU | 508984 A1 | 8/1979 |
| WO | 2015130821 | 9/2015 |
| WO | 2015200875 A1 | 12/2015 |
| WO | 2018005796 A1 | 1/2018 |

OTHER PUBLICATIONS

Gaasterland, et al., "Initial Experience with a New Method of Laser Transscleral Cyclophotocoagulation for Ciliary Ablation in Severy Galucoma", Trans Am Ophthalmol Soc., vol. 90, 1992, pp. 225-246.

Goel, et al., "Aqueous Humor Dynamics: A Review", The Open Ophthalmology Journal, vol. 4, Sep. 3, 2010, pp. 52-59.

Kosoko, et al., "Long-Term Outcome of Initial Ciliary Ablation with Contact Diode Laser Transscleral Cyclophotocoagulation for Severe Glaucoma", Ophthalmology, vol. 103, No. 8, Aug. 1996, pp. 1294-1302.

Shields, "Surgical Anatomy", Glaucoma Surgery, Harvard Medical School, Massachusetts Eye and Ear Infirmary, Boston, Massachusetts, Mosby Year Book, 1992, 5 pages.

Tan, et al., "Mircopulse Transscleral Diode Laser Cyclophotocoagulation in the Treatment of Refractory Glaucoma", Clinical and Experimental Ophthalmology, vol. 38, No. 3, Apr. 2010, pp. 266-272.

IRIDEX, "G-Probe™ Operator Manual", 13105-EN Rev D 2013-05, 17 pages.

Allingham, et al., "Probe Placement and Power Levels in Contact Transscleral Neodymium:YAG Cyclophotocoagulation", Arch Ophthalmology, vol. 108, No. 5, May 1990, pp. 738-742.

Beckman, et al., "Transscleral Ruby Laser Irradiation of the Ciliary Body in the Treatment of Intractable Glaucoma", Trans Am Acad Ophthalmol Otolaryngol, vol. 76, No. 2, Mar.-Apr. 1972, pp. 423-436.

Schuman, et al., "Laser Cyclophotocoagulation", International Ophthalmology Clinics, vol. 30, No. 2, Spring 1990, pp. 111-119.

CONTACT PROBE FOR THE DELIVERY OF LASER ENERGY

CROSS-REFERENCES TO RELATED APPLICATIONS

The present application is a Continuation of U.S. patent application Ser. No. 17/465,405 filed Sep. 2, 2021 (Allowed); which is a Continuation of U.S. patent application Ser. No. 16/369,477 filed Mar. 29, 2019 (now U.S. Pat. No. 11,116,666); which is a Continuation of U.S. patent application Ser. No. 14/579,783 filed Dec. 22, 2014 (now U.S. Pat. No. 10,292,868); which is a Continuation of U.S. patent application Ser. No. 12/261,889 filed Oct. 30, 2008 (now U.S. Pat. No. 8,945,103); which claims priority to U.S. Provisional Appln. No. 60/983,811 filed Oct. 30, 2007; the full disclosures which are incorporated herein by reference in their entirety for all purposes.

BACKGROUND OF THE INVENTION

Field of the Invention. The present invention is directed generally to medical devices, systems, and methods, particularly for treatment of an eye. In particular, embodiments of the present invention are directed toward contact probes for the delivery of laser energy, and more particularly to contact probes that are used for lowering the intraocular pressure (IOP) in human eyes afflicted with glaucoma. Even more specifically, the present invention is directed toward laser therapy for lowering IOP in glaucomatous eyes via transconjunctival/transscleral ab-externo treatment with infrared laser energy directed to pigmented intraocular cells of the pars plana and/or the posterior portion of the pars plicata.

Glaucoma is a leading cause of blindness. Glaucoma involves the loss of retinal ganglion cells in a characteristic pattern of optic neuropathy. Untreated glaucoma can lead to permanent damage of the optic nerve and resultant visual field loss, which can progress to blindness. The loss of visual field due to glaucoma often occurs gradually over a long time and may only be recognized when the loss is already quite advanced. Once lost, this damaged visual field can never be recovered.

Raised intraocular pressure (IOP) is a significant risk factor for developing glaucoma. IOP is a function of production of liquid aqueous humor by the ciliary body of the eye and its drainage through the trabecular meshwork. Aqueous humor is a complex mixture of electrolytes, organics solutes, and other proteins that supply nutrients to the non-vascularized tissues of the anterior chamber of the eye. It flows from the ciliary bodies into the posterior chamber, bounded posteriorly by the lens and the ciliary zonule and bounded anteriorly by the iris. Aqueous humor then flows through the pupil of the iris into the anterior chamber, bounded posteriorly by the iris and anteriorly by the cornea. In the conventional aqueous humor outflow path, the trabecular meshwork drains aqueous humor from the anterior chamber via Schlemm's canal into scleral plexuses and the general blood circulation. In open angle glaucoma there is reduced flow through the trabecular meshwork. In angle closure glaucoma, the iris is pushed forward against the trabecular meshwork, blocking fluid from escaping.

Uveoscleral outflow is a non-conventional pathway that is assuming a growing importance in the management of glaucoma. In uveoscleral outflow, aqueous humor enters the ciliary muscles from the anterior chamber and exits through the supraciliary space and across the anterior or posterior sclera. Uveoscleral outflow may contribute significantly to total aqueous humor outflow.

Currently, glaucoma therapies aim to reduce IOP by either limiting the production of aqueous humor or by increasing the outflow of aqueous humor. Medications such as beta-blockers, carbonic anhydrase inhibitors, etc., are used as the primary treatment to reduce the production of aqueous humor. Medications may also be used as the primary therapy to increase the outflow of the aqueous humor. Miotic and cholinergic drugs increase the trabecular outflow, while prostaglandin drugs, for example, Latanoprost and Bimatoprost, increase the uveoscleral outflow. These drugs, however, are often expensive, may have undesirable side effects, and may have compliance-dependent efficacy which diminishes over time.

Surgery may also be used to increase its outflow or to lower the production of aqueous humor. Laser trabeculoplasty is the application of a laser beam to irradiate areas of the trabecular meshwork to increase fluid outflow. Cyclocryotherapy and laser cyclophotocoagulation are surgical interventions to lower the production of aqueous humor.

These surgical interventions work by permanently destroying the ciliary body and related processes. Although they may be effective, these surgical interventions are normally used as a last resource in the management of glaucoma due to the risk of the severe complication of phthisis bulbi—the often painful and unsightly atrophy and degeneration of an eye. Other adverse side effects may include ocular hypotony and inflammation of the anterior eye segment, which may be associated with an increased incidence of macula complications. Still other adverse side effects include transiet hyphaema and exudates in the anterior chamber, uveitis, visual loss, and necrotizing scleritis.

In laser transscleral cyclophotocoagulation, a continuous train of high intensity infrared laser energy is directed toward selected portions of the pars plicata region of the ciliary body, structures under the overlying conjunctiva and scleral layers. Selected portions of the ciliary body and related processes are permanently destroyed, thereby decreasing aqueous humor formation. Laser energy may be delivered through the air by free beams directed through air to a patient seated at a special slit lamp. Alternatively, laser energy may be delivered through the use of fiber optic handpieces placed in contact with the patient's eyeball. In both laser energy delivery methods, however, accurately aiming a laser toward a ciliary body of the eye can be challenging for a surgeon. Thus, contact handpiece probes (for example, the G-Probe available through IRIDEX Corporation of Mountain View, CA and described in U.S. Pat. No. 5,372,595, the full disclosure of which is incorporated herein by reference in its entirety) have been designed to facilitate the aiming of a laser toward the pars plicata region of the ciliary body. The G-Probe, for example, has special contours that facilitate consistent placement of the probe relative to landmark structures of the eye, thereby decreasing the likelihood of incidental laser exposure to unintended structures. However, the permanent destruction of portions of the ciliary body and the potential for phthisis bulbi and other adverse side effects remains unavoided. The potential pain associated with such treatments also generally justifies localized delivery of pain relieving agents to the posterior portion of the eye. Though alternative and potentially advantageous laser treatments have been proposed, they have not been shown to provide long-term benefits, thereby limiting their use.

In light of the above, there is a need for laser-based methods and devices for the treatment of glaucomatous eyes which avoid many of the shortcomings described above.

BRIEF SUMMARY OF THE INVENTION

Embodiments of the present invention provide systems, devices, and methods for treating an eye, in particular examples, a glaucomatous eye. An amount of pulsed laser energy is delivered to the pars plana of the eye by a hand-holdable device. This device comprises a hand-holdable elongate member and a contact member disposed on an end of the elongate member. A contact surface of the contact member is placed in direct contact with the eye so that a reference edge of the contact member aligns with a reference feature of the eye, usually the limbus, and a treatment axis defined by the elongate member forms a predetermined, non-zero angle with the optical axis of the eye. Typically, amounts of pulsed laser energy are transmitted to a circumferential series of tissue regions of the eye. The delivered pulsed laser energy is insufficient to effect therapeutic photocoagulation but is sufficient to increase uveoscleral outflow so as to maintain a reduction from pre-laser treatment intraocular pressure. Thus, permanent destruction of tissue structures in the eye and undesired thermal damage of adjacent tissue structures, both of which typically result from conventional laser cyclophotocoagulation procedures, is avoided while significant degrees of intraocular pressure reduction are, surprisingly, maintained for long periods.

Accordingly, an object of the present invention is to provide an improved laser energy delivery handpiece.

Another object of the present invention is to provide a laser energy delivery handpiece with a handpiece axis that is substantially perpendicular to the eye.

Another object of the present invention is to provide a laser energy delivery handpiece that has a contact surface with a single radius of curvature across the contact surface.

Still another object of the present invention is to provide a laser energy delivery handpiece that has a contact surface with substantially no sharp edges.

A further object of the present invention is to provide a laser energy delivery handpiece with a contoured contact surface and a protruding hemispherical laser output tip.

Still a further object of the present invention is to provide a laser energy delivery handpiece.

Another object of the present invention is to provide a laser energy delivery handpiece that allows the surgeon to precisely target the intended intraocular structures, such as the pars plana and pars plicata, and avoid misdirected applications by positioning it over the sclera in reference to a stable external anatomical landmark such as the limbus.

A further object of the present invention is to provide a laser energy delivery handpiece that helps a surgeon to keep the direction of the laser beam precisely pointed toward the internal intraocular, invisible target.

Yet another object of the present invention is to provide a laser energy delivery handpiece that allows delivery of treatment either with a series of individual precisely-spaced applications and/or with continuously sliding 180° or 360° arc motions.

Still another object of the present invention is to provide a laser energy delivery handpiece that allows the surgeon to keep a consistent scleral indentation in order to maximize the transmission of the laser energy through the conjunctiva-sclera layers, and to minimize the variations of the divergence of the laser beam reaching the targeted ciliary body structures, from the posterior pars plicata through the pars plana.

These and other objects of the invention are achieved in a laser energy delivery handpiece characterized by an axis and adapted to receive a fiber optic for laser surgery on a patient's eye. The eye has a shaped sclera, a limbus and an optic axis. Portions define a contact surface that conforms to the shape of the sclera at the limbus when the axis of the handpiece forms a predetermined angle relative to the external surface of the eye. The contact surface conforms to the shape of the sclera at the limbus when the axis of the handpiece is substantially perpendicular to the eye.

In another embodiment of the present invention, a laser energy delivery handpiece receives a fiber optic for laser surgery on an eye and has an input end, an output end, a top, a bottom and sides. The fiber optic has an optic axis. The eye has a shaped sclera, limbus, and an optic axis. The handpiece includes a body for holding the fiber optic and a contoured end portion. The contoured end portion has an end surface with an opening for the fiber optic. The end surface conforms to the shape of the sclera at the limbus when the optic axis of the fiber optic is substantially perpendicular to the eye.

An aspect of the invention provides a laser treatment method for an eye, the eye having a pars plana posterior to a pars plicata and a pre-laser treatment intraocular pressure. An amount of pulsed laser energy is delivered to the pars plana of the eye. The amount is insufficient to effect therapeutic photocoagulation and is sufficient to increase uveoscleral outflow so as to maintain a reduction from the pre-laser treatment intraocular pressure. Typically, the amount is sufficient to maintain the reduction from the pre-laser treatment intraocular pressure more than 5 months after the pulsed laser energy is delivered. The amount of energy will typically be delivered without direct posterior eye pain alleviating agent delivery, and without excessive pain.

Generally, a laser delivery tip of a probe is positioned in contact with an outer surface of the eye and the amount of pulsed laser energy is delivered from the positioned probe so that the pulsed laser energy is oriented toward a first pars plana region and such that permanent thermal damage to the pars plicata is avoided. The eye has an optical axis, and the probe will typically be oriented so that the pulsed laser energy is angularly offset from the optical axis when the tip of the probe is positioned in contact with the surface of the eye. The probe may define a treatment axis along which the pulsed laser energy is delivered, and the probe will typically be positioned so that the treatment axis is generally perpendicular with the surface of the eye when the tip of the probe is positioned in contact with the surface of the eye.

To position the tip of the probe in contact with the surface of the eye, a reference structure of a contact surface of the probe may be positioned in alignment with a reference feature of the eye. The laser delivery tip will be disposed along the contact surface so that the pulsed laser energy is posterior to a limbus of the eye by over 2 mm. The first pars plana region to where the pulsed laser energy is delivered may be posterior to the limbus by over 3 mm. The reference feature of the eye will typically comprise the limbus, and the reference structure of the contact surface will typically comprise an edge separated from the laser delivery tip by over 2 mm. The edge extends between opposed lateral placement sides of the contact surface. The pulsed laser energy is delivered to the first pars plana region while the probe is held at a fixed position against the eye. The probe may be incrementally moved laterally, with reference to the sides of the contact surface, along the limbus so as to sequentially treat a plurality of circumferentially offset regions of the pars plana. The offset regions define angular widths about the ocular axis of from 5 to 20 degrees. The pulsed laser energy may be delivered to the first pars plana region for at least about 1 second.

The pulsed laser energy will generally comprise pulsed infrared laser energy, for example, laser energy having a wavelength of 810 nm. The total laser energy directed to the pars plana will generally be less than 75 J. In some embodiments, the pulsed laser energy may be delivered from a plurality of fixed probe locations. Each pulse will typically have an energy of less than 1 mJ, and total laser energy directed to the pars plana may be less than 40 J. The pulsed laser energy will typically have a duty cycle of about 50% or less, or even a duty cycle of about 20% or less.

In many embodiments, a first portion of the pulsed laser energy is directed to a first arc about the optical axis of the eye. The first arc will typically be disposed on a superior region of the eye. A second portion of the pulsed laser beam may be directed toward a second arc about the optical axis of the eye, the second arc being spaced away from the first arc and disposed along an inferior region of the eye.

In some cases, the tip of the probe may be positioned in contact with the surface of the eye by sliding the tip of the probe in alignment with the pars plana during delivery of the pulsed laser energy.

Another aspect of the invention provides a method of reducing excessive intraocular pressure in an eye. A pulsed laser beam is transmitted to a circumferential series of tissue regions of an eye by the following steps. A tip of a probe is positioned in contact with the surface of the eye in a position at least 3 mm posterior of the limbus. The pulsed laser beam is directed from the positioned tip of the probe from the position toward an associated tissue region of the eye such that associated tissue region is treated and the coagulation within the eye is inhibited. The tip of the probe is repositioned in contact with the surface of the eye in another position disposed at least 3 mm posterior of the limbus and circumferentially offset from the treated region about an optical axis of the eye and the pulsed laser beam is again directed from the probe to an associated tissue region until the circumferential series of tissue regions have been treated. The pulsed laser beam is delivered while the probe is maintained at each of the positions toward the associated tissue regions of the eye such that an aggregate amount of the pulsed laser beam delivered to the tissue regions alleviates the excessive intraocular more than five months after the tissue regions have been treated.

Another aspect of the invention provides a method for treating an eye by reducing intraocular pressure. A tip of a probe is positioned in contact with the surface of the eye so that the tip of the probe is posterior the limbus of the eye by a desired distance. The tip of the probe is moved across the surface of the eye while the tip of the probe is maintained at the desired distance posterior the limbus of the eye. Pulsed laser energy is delivered toward a region of the eye posterior to the limbus while the tip of the probe is slid across the eye and maintained in contact with the surface of the eye.

Another aspect of the invention provides a hand-holdable device for delivering optical energy to treat an eye. The device comprises a hand-holdable elongate member and a contact member disposed on an end of the elongate member. The hand-holdable elongate member defines a treatment axis and is adapted to receive an optical fiber for delivering optical energy along the treatment axis. The contact member comprises a reference element and defines a contact surface. The contact surface is placed in direct contact with the eye and the reference element is aligned with a reference feature of the eye. The contact surface conforms to a region of the surface of the eye and the treatment axis forms a predetermined, non-zero angle with the optical axis of the eye.

The contact surface can be placed in direct contact with the eye and the reference element can be aligned with a reference feature of the eye such that the treatment axis is perpendicular to the surface of the eye.

The contact surface will typically conform to the shape of the sclera of the eye at the limbus of the eye when the contact surface is placed in direct contact with the eye and the reference element is aligned with the reference feature of the eye.

The device may further comprise an optical energy source coupled to the elongate member. The delivered optical energy may comprise light energy from one or more light emitting diodes of the optical energy source. Typically, the delivered optical energy may comprise light energy from one or more lasers of the optical energy source. The delivered optical energy may be pulsed and have a duty cycle of about 50% or less or even about 20% or less.

The hand-holdable device will typically be adapted to deliver optical energy to a region of the eye posterior to the limbus when the contact surface is placed in direct contact with the eye and the reference element is aligned with a reference feature of the eye. The region of the eye posterior to the limbus may be selected from the group consisting of the pars plana of the eye, the pars plana—pars plicata junction of the eye, and the posterior portion of the pars plicata of the eye.

The contact surface of the contact member may define a protruding optical energy delivery tip disposed along the treatment axis.

Typically, the reference feature comprises a reference edge shaped to conform with the outer edge of the limbus of the eye.

An optical energy output aperture may be spaced away from the reference edge by at least about 3 mm to facilitate optical irradiation over at least one of the pars plana of the eye, the pars plana—pars plicata junction, and the posterior portion of the pars plicata of the eye.

In many embodiments, the contact surface may comprise a first side relief and a second side relief opposite the first side relief. The first side relief and the second side relief are adjacent the reference element of the contact surface with a width of the contact surface therebetween. The width of the contact surface is sized to contact a treatment region of the eye along a plurality of circumferentially adjacent treatment regions forming an arc centered about the optical axis of the eye. The circumferentially adjacent treatment regions spaced apart from each other by from 5° degrees to 30° degrees, for example, by about 10° degrees.

Another aspect of the invention provides a device for delivering optical energy to treat an eye, the eye having a pars plana. The device comprises a handpiece, a contact member, and a laser tip. A contact member is disposed on an end of the handpiece. The contact member comprises a target tissue reference element and a treatment site spacing reference element and defines a contact surface. The laser delivery tip is adapted to couple with an optical energy source. The laser delivery tip is positioned relative to the target tissue reference element such that when the contact surface is placed in direct contact with an outer surface of the eye with the target tissue reference element aligned with a reference feature of the eye and optical energy is delivered from the laser delivery tip, the optical energy is directed toward the pars plana at an associated treatment site. The laser delivery tip is positioned relative to the treatment site spacing reference element such that a circumferential series of treatment sites are defined when the contact surface is repeatedly placed in direct contact with an outer surface of the eye with the target tissue reference element aligned with a reference feature of the eye and the treatment site spacing reference element aligned with a feature of a prior treatment and delivering an amount of pulsed laser energy to the pars plana of the eye at an associated treatment site. Delivery of an amount of pulsed laser energy from the circumferential series of treatment sites to the pars plana that is insufficient to effect therapeutic photocoagulation can be sufficient to increase uveoscleral outflow so as to maintain a reduction from the pre-laser treatment intraocular pressure.

In another aspect of the invention, a handpiece which is adapted to direct and deliver optical energy in a predetermined direction and is suitable for delivery of optical energy to a patient's eye is provided. The predetermined direction is defined as the optical axis of the handpiece. The eye has a shaped sclera, a cornea, a limbus, and an optical axis. The handpiece incorporates pieces, portions or features that aid in the repeatable application of the handpiece with respect to certain features of the patient's eye. These reference features may be either permanent or temporary. They are provided with respect to treatment angle or direction of the optical output axis, with the treatment axis essentially not parallel to the optical axis of the patient's eye. They may be provided with one or more of the following parameters: locational position, indentation pressure, or depth spacing between discrete treatment sites.

In many embodiments, the method of delivery of optical energy from its source to its treatment target includes one or more optical fibers.

In many embodiments, the source of optical energy delivered is intended to be one or more lasers.

In many embodiments, the source of optical energy delivered is intended to be one or more light emitting diodes (LEDs).

In many embodiments, the treatment angle/direction is essentially normal, i.e., perpendicular, to the reference surface. The reference surface may be, for example, the sclera or the cornea.

In many embodiments, the feature facilitating placement with respect to a reference surface is one or more curves or facets approximating a portion of a sphere. The feature facilitating placement with respect to a reference surface may be one or more curves or facets approximating a portion of a concave sphere.

In many embodiments, the locational reference is at least partly derived from the limbus, i.e., the ocular region of intersection and transition between the corneal and scleral curves.

In many embodiments, the specific dimensional reference from the limbus is 0 to 4 mm, and may be in a direction anterior or posterior to the limbus.

In many embodiments, the reference for indentation depth or pressure is at least partly derived from the scleral surface.

In many embodiments, the indentation depth measured from the reference surface in its natural position is between 0 and 1.5 mm.

In many embodiments, the reference for indentation depth or pressure is at least partly derived from the corneal surface.

In many embodiments, the reference for spacing between adjacent treatment sites is at least partly derived from one or more previous treatment sites. The spacing between adjacent treatment sites may be such so as to permit 1 to 6 application sites per clock-hour, i.e., 5 to 30 degree angular spacing, or 12 to 72 sites per full treatment circumference.

DETAILED DESCRIPTION OF THE INVENTION

Figure 1:
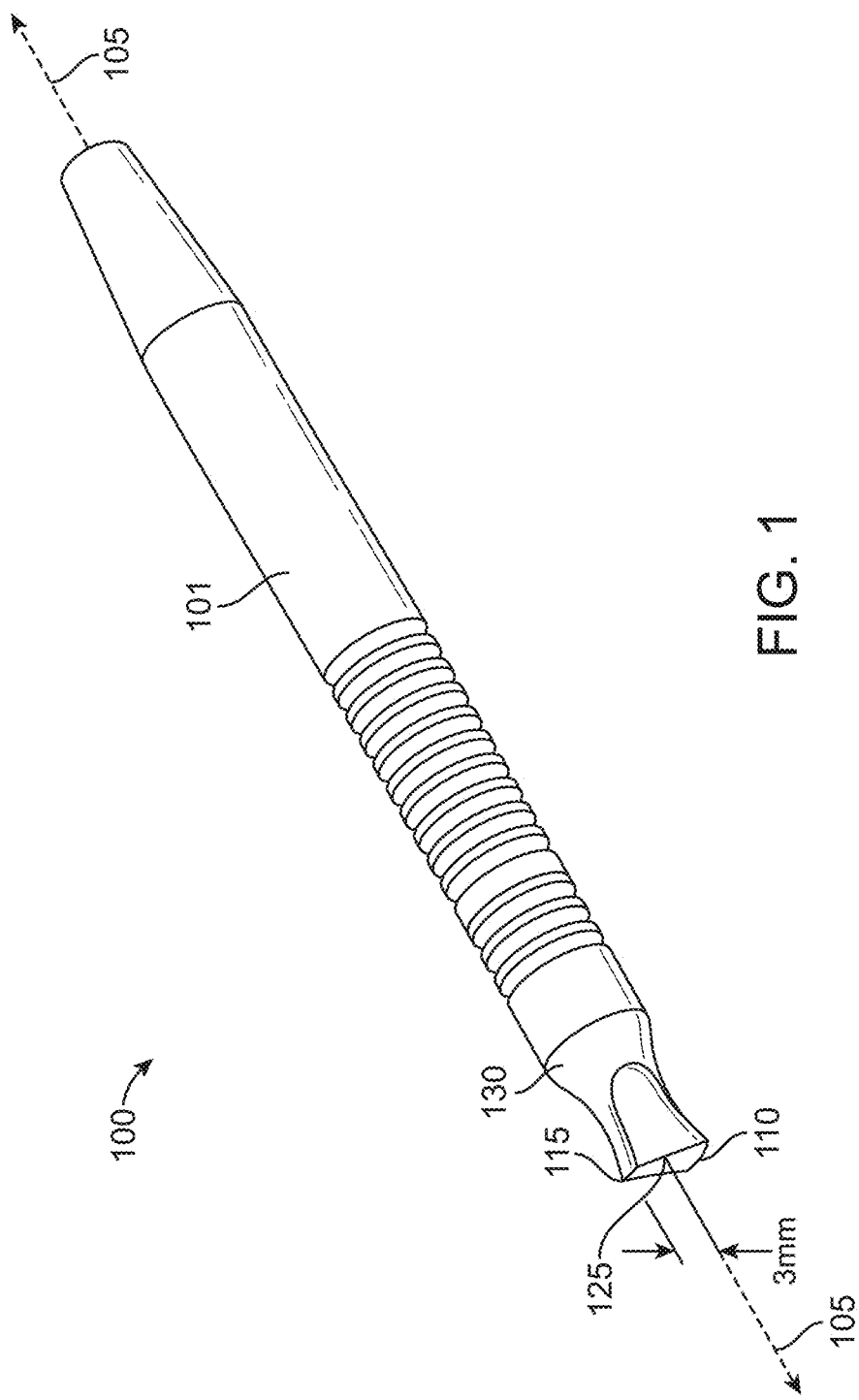
FIGS. 1, 2 and 4 illustrate various embodiments of a contact probe of the present invention.

In embodiments of the present invention, a laser energy delivery handpiece 100 is provided that is specifically designed for the efficient transconjunctival/transscleral delivery of laser energy, for example, infrared laser energy from a pulsed 810 nm diode laser, over the posterior region of the pars plicata, over the pars plana-pars plicata junction, and/or over the pars plana. Optical energy from other sources, for example, light emitting diodes (LEDs), may be delivered as well.

A footprint contact surface 110 of the handpiece 100 is designed so that a fiber optic 120 coupled to the handpiece 100 has a protruding hemispherical tip 125 that is about 3 mm posterior to the limbus at any 360° location, when in normal contact with the conjunctiva/sclera and with the small radius next to the limbus, in particular, the outer edge of the limbus.

The footprint contact surface 110 is designed to ensure a radial orientation of the laser beam so that the laser energy is always directed substantially perpendicular to the conjunctiva/sclera point of indentation.

In various embodiments, the laser beam output tip 125 protrudes from 0.25 mm to 1.0 mm, preferably 0.75 mm, beyond the contact surface.

The indentation of the laser beam output tip 125 maximizes the transmission of infrared laser energy through the conjunctiva and sclera and provides the beam divergence to irradiate all ciliary body structures from the anterior (pars plicata) through the posterior (pars plana) portions of the ciliary body.

The footprint contact surface 110 is designed to allow the surgeon to administer the treatment either with a continuously 360° sliding motion over the conjunctiva overlying the pars plana or, with a series of individual applications with precisely defined angular spacing or radial displacements.

The footprint contact surface 110 can provide a radial displacement of 5° or 10° or 20°, and the like for a treatment density over a 360° radial area at the treatment site with, 72 or 36 or 18 applications respectively. In some embodiments, a lateral edge 160 to an indentation mark of the laser beam output tip 125 spaces each application by 10° over the sclera and allows 36 individual applications in the 360° radial treatment area.

In some embodiments, the footprint contact surface 110 slides around the treatment area while the laser continuously delivers laser energy as opposed to individual spaced applications described in the previous embodiment.

The continuously emitted laser energy that is delivered while the footprint contact surface slides over the sclera can be seen as a paint delivered with a sliding brush.

Both modalities of the prior paragraph are intended to treat the area of pigmented ciliary body epithelium cells as defined by the surgeon. When applied ab-externo with continuously sliding motion, for example in two steady strokes, with an upper 180° in one move and the lower 180° in another move, a low power pulsed laser emission is "painted" over the ciliary body. This provides an irradiation for all the ciliary body epithelium cells in a movement analogous to a paintbrush of photothermal energy sweeping over the eyeball with the power and sweeping time determined by the surgeon.

FIG. 1 illustrates a laser energy delivery handpiece 100 according to embodiments of the present invention. Laser energy delivery handpiece 100 comprises an elongate body 101 and an end portion 130 disposed on one end of the elongate body 101. Laser energy delivery hand piece 100 defines a treatment axis 105 and is adapted to receive a fiber optic 120 for laser surgery on a patient's eye E. The eye E has a shaped sclera, a limbus and an optical axis 200. End portion 130 of the laser energy delivery handpiece 100 define a contact surface 110 that conforms to the shape of the sclera at the limbus when the axis 105 of the handpiece forms a predetermined angle 600 relative to the optical axis 200 of the eye E. The contact surface 110 conforms to the shape of the sclera at the limbus when the axis of the handpiece 100 is substantially perpendicular to the conjunctiva-sclera point of indentation of the eye E.

The contact surface 110 may have a single radius of curvature across the contact surface 110 and no sharp edges.

In some embodiments of the present invention, the laser energy delivery handpiece 100 has an input end, an output end, a top, a bottom and sides. Elongate body 101 holds the fiber optic 120 and end portion 130 is contoured.

In some embodiments, the footprint of the contact surface 110 shows the position of a protruding hemispherical laser beam output tip 125, or other non-blunt geometry, with respect to a limbal placement edge 115, e.g., the short side of the contact surface 110. Limbal placement edge 115 has a contact surface contour that conforms to the limbus and is generally circularly concave with a radius of about 5.25-6.0 mm. The laser beam output tip 125 is, in many embodiments, at 3.0 mm distance from the limbal placement edge 115 to facilitate the optimal irradiation over the eye's pars plana—pars plicata junction and/or over the eye's pars plana, from the limbus 20 points to the anterior portion of the pars plana in the normal anatomy of the human eye as illustrated in FIG. 3.

The two lateral placement contoured edges 160, e.g., the longer sides of the footprint, indicate a 5°-20°, and more particularly a 10° radial displacement from the laser beam output tip 125. The edges 160 may comprise side reliefs, one on each edge, extending from contact surface 110. Also, the edges 160 may each define lines which intersect at the center of curvature of limbal placement edge 115.

Figure 2:
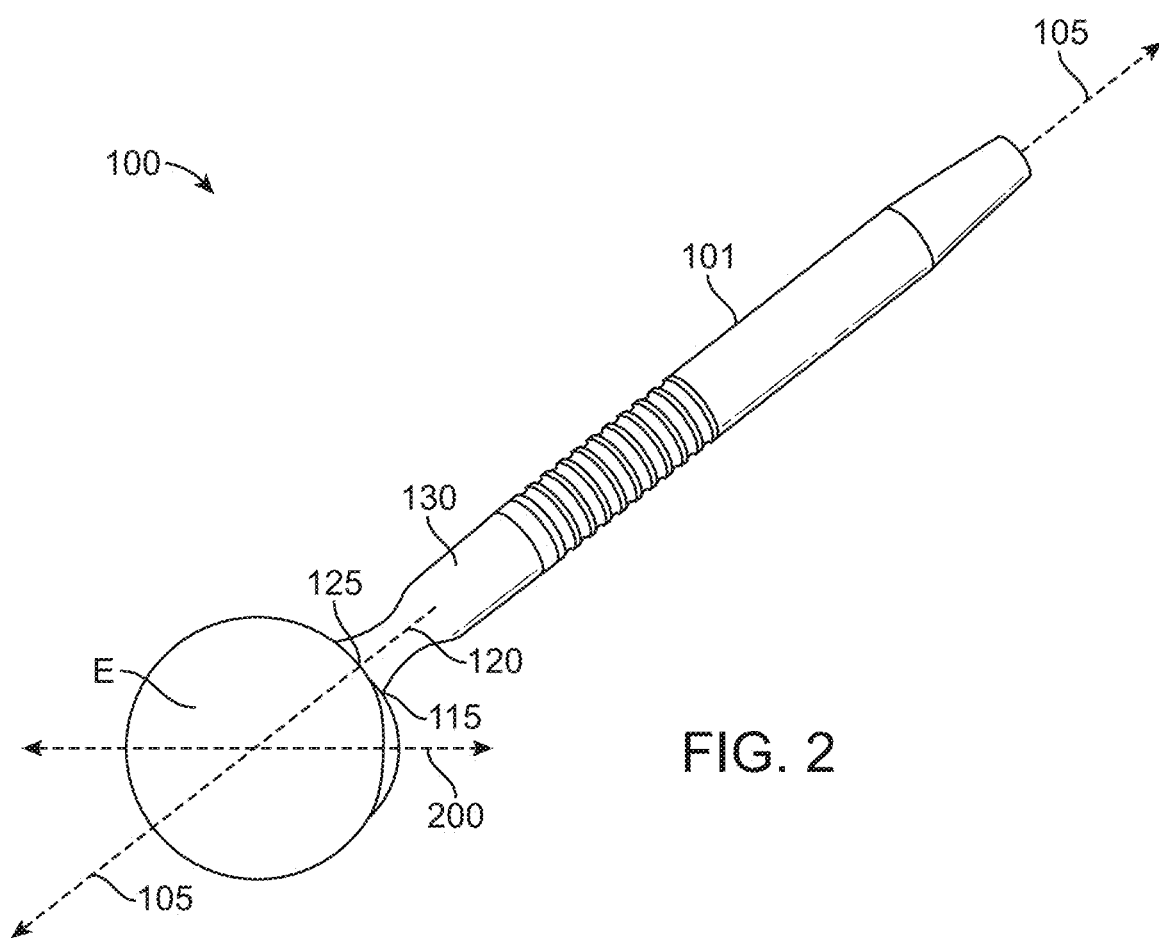

FIG. 2 shows the laser energy delivery handpiece 100 positioned against the eye E with the short limbal placement edge 115 next to the limbus and directing the laser energy radially to the eyeball center over the pars plana—pars plicata junction, generally indicated by the axis 105. Alternatively, the distance between short limbal placement edge 115 and tip 125 will be such that the laser energy is directed to the eyeball center over the pars-plana or any structure posterior the limbus.

Figure 3:
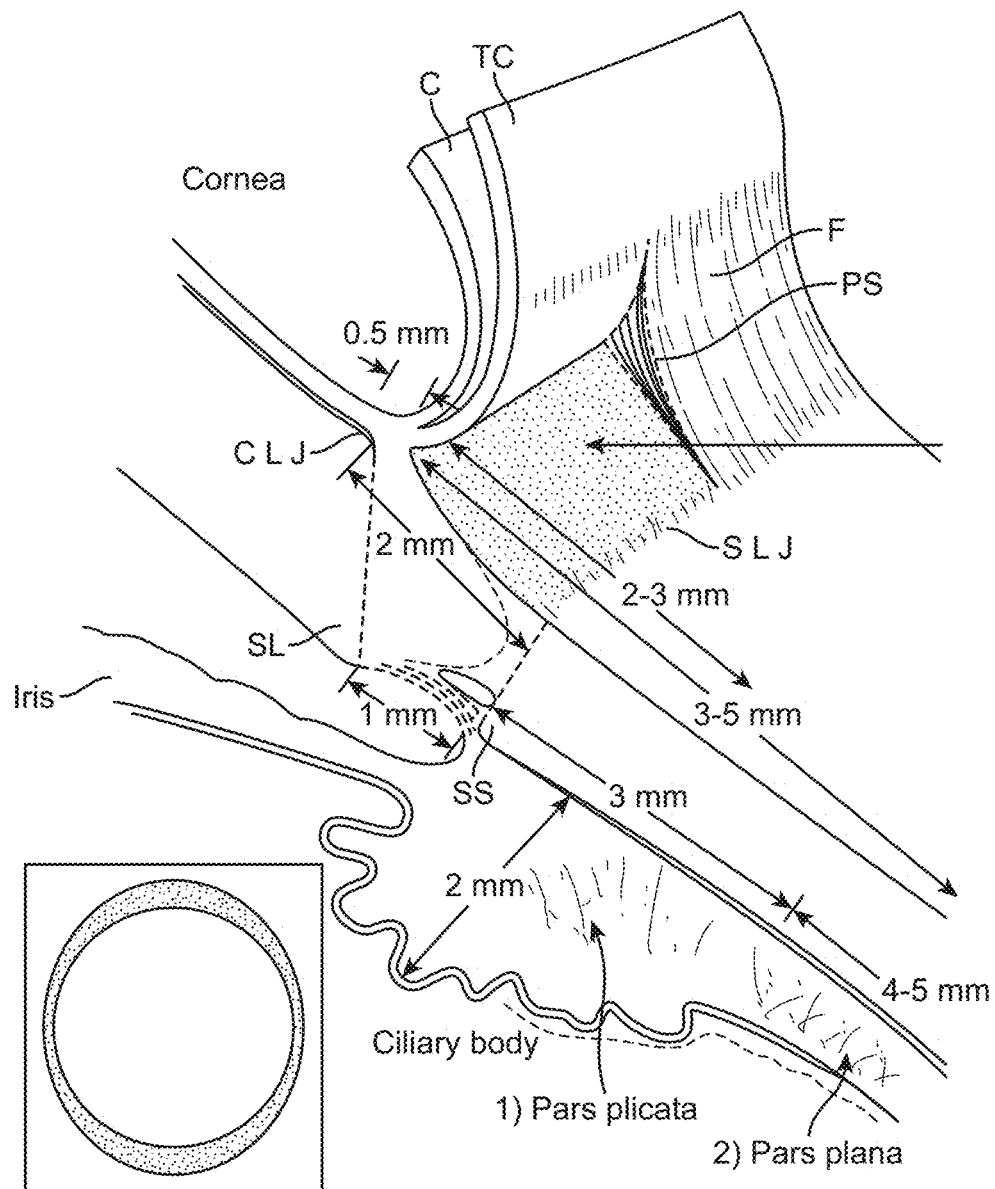
FIG. 3 illustrates elements of the eye in relation to a contact probe of the present invention.
Figure 4:
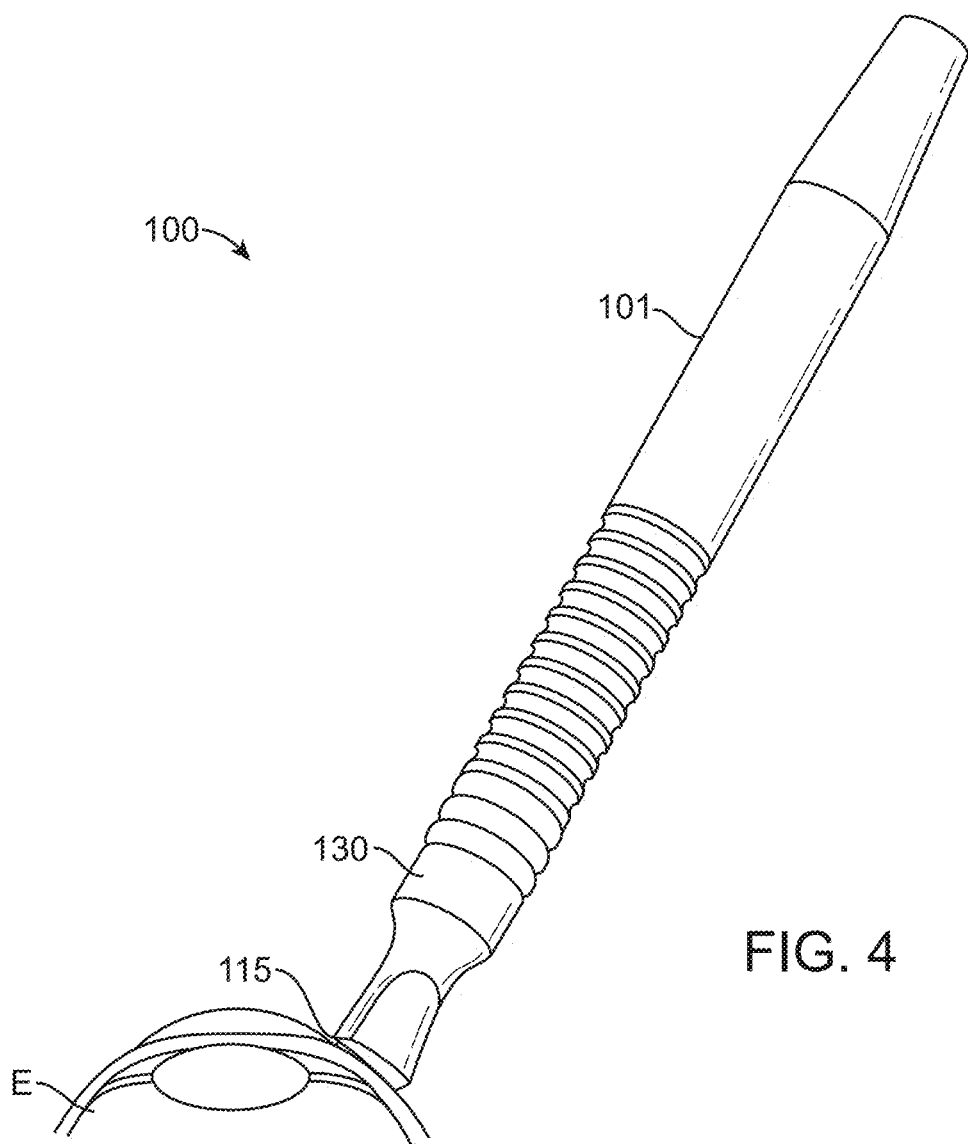

FIG. 3 shows the surgical eye anatomy relevant to the handpiece. This laser therapy may target the cilary body that spans from the posterior pars plicata to the pars plana. Alternatively, the pars plana may be targeted and the pars plicata, ciliary body, and other ciliary processes avoided. The short limbal placement edge 115 is always kept next to the external limbus line (CU cornea-limbus junction). In this way, protrusion of the laser output tip 125, which is about 3 mm posterior the limbus, directs a diverging beam that irradiates a large portion of the ciliary body in the posterior pars plicata and in the pars plana. Alternatively, the laser output tip 125 may be spaced away from the short limbal placement edge 115 such that laser output tip 125 directs a diverging beam that irradiates the pars plana while avoiding the pars plicata, ciliary body, and other ciliary processes.

Figure 5:
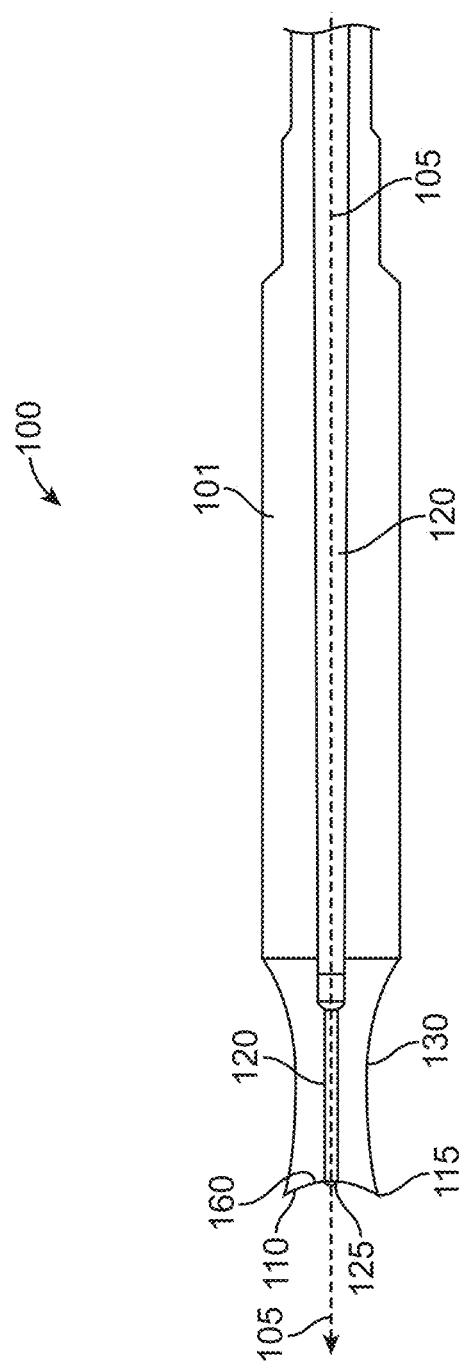
FIG. 5 shows a cross section of a contact probe according to embodiments of the present invention.
Figure 5A:
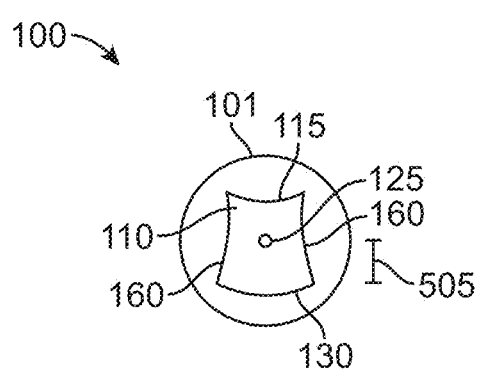
FIG. 5A shows a front view of a contact probe according to embodiments of the present invention.

FIG. 5 shows a cross section of laser energy delivery handpiece 100. Laser energy delivery handpiece 100 comprises elongate body 101 and end portion 130. Handpiece 100 defines treatment axis 105 and houses fiber optic 120 so that fiber optic 120 directs optical energy along treatment axis 105. End portion 130 comprises a contoured surface 110 having a radius of curvature shaped to conform with the shape of the sclera of the limbus of the eye when surface 110 is placed in contact with the surface of the eye E. As shown in FIG. 5A, contoured surface 110 comprises lateral edges 160 and a limbal placement edge 115. Laser energy is delivered from protruding tip 125 protruding from contoured surface 110. Protruding tip 125 is spaced away from limbal reference edge 115 at a predetermined distance, usually about 3 mm, e.g., 3.4 mm, from limbal reference edge 115. The limbus of the eye E can serve as a reference point for the placement of handpiece 100. Limbal reference edge 115 is placed adjacent the outward facing edge of the limbus such that opening 125 directs laser energy over the pars plana and/or pars plana—pars plicata junction and treatment axis 105 is parallel to the surface of the eye.

Figure 6A:
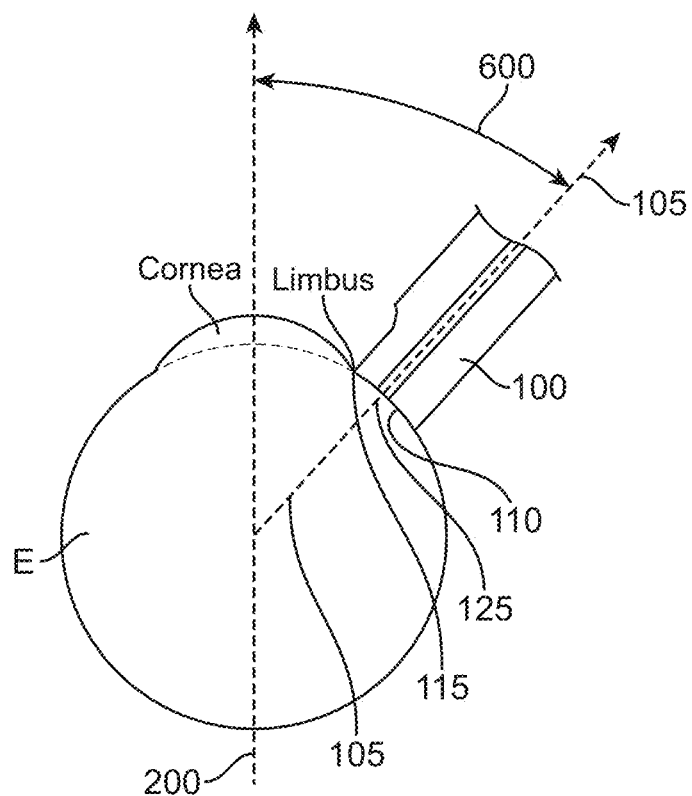
FIGS. 6A-6E shows a method of treating the eye using a contact probe according to embodiments of the present invention.

FIGS. 6A-6E show an exemplary method of using laser eye delivery handpiece 100 to delivery laser energy to treat an eye. As shown in FIG. 6A, handpiece 100 is positioned at a first treatment region so that contoured surface 110 is in contact with the sclera of the eye E and limbal reference edge 125 is adjacent the limbus, the region of the eye between the cornea and the sclera. Treatment axis 105, as defined by handpiece 100, forms a predetermined angle, for example, a 40° degree angle, with optical axis 200 of the eye E. Tip or opening 125 is spaced posterior the limbus with a distance 505 which may be, for example, about 3 mm. Laser energy is directed through tip or opening 125 to direct laser energy to the pars plana.

In an exemplary embodiment, the directed laser energy comprises pulsed laser energy from an infrared laser that can be operated in pulsed as well as continuous wave emission modes. For example, the pulsed continuous wave infrared laser has about a 30% duty cycle, with an "on" time of about 500 μs and an "off" time of about 1100 μs, about a 15% duty cycle, with an "on" time of about 300 μs and an "off" time of about 1700 μs, or about a 10% duty cycle, with an "on" time of about 200 μs and an "off" time of about 1800 μs. Pulsed laser energy can avoid undesired thermal damage to a target by allowing the target to cool during the "off" time of the laser before the next pulse of laser energy is delivered during the "on" time. The duty cycle may be selected so that cumulative thermal buildup, caused by insufficient cooling during the "off" time of the laser beam, is avoided. Thus, laser damage can be reduced to a minimum level sufficient to trigger a biological response needed for lowering of intraocular pressure (IOP).

In the exemplary procedure described with reference to FIGS. 6A-6E, a duty cycle of 15% is used. The power of the laser is set at 1500 mW and the duration of irradiation for each spot is 300 ms.

Figure 6B:
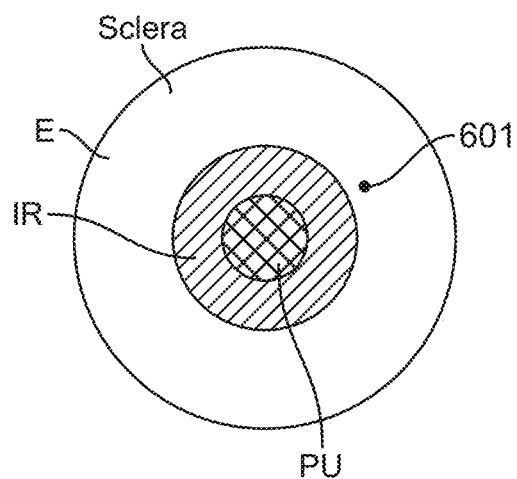

As shown in FIG. 6B, laser energy is directed toward a first spot 601. Afterwards, handpiece 100 is repositioned, for example, by moving handpiece 100 over, to a second treatment region adjacent the first treatment region. Handpiece 100 may be moved by sliding it over to the second treatment region from the first treatment region while maintaining contact surface 110 in contact with the surface of the eye. Or, handpiece 100 may be removed from contact from the surface of the eye at the first position and placed in contact with the eye again at the second position. Edges 160 may have side reliefs which may indent the surface of the eye, with the indentations providing a reference to help reposition handpiece 100. At the second position, handpiece 100 is again positioned so that limbal reference edge 125 is adjacent the limbus.

Figure 6C:
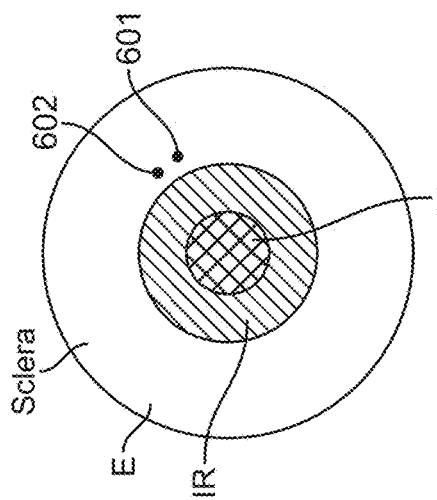

As shown in FIG. 6C, laser energy is directed toward a second spot 602. Thus, first spot 601 and second spot 602 are equidistant from the optical axis 200 of the eye E. This process of repositioning handpiece 100 and directing laser energy toward the pars plana is repeated for a third spot, a fourth spot, and so forth. For example, as shown in FIG. 6D, laser energy is directed toward a first treatment point at 320° on a right eye, then toward a second treatment point at 330°, and then successively clockwise every 10° until a point at 90°, e.g., toward points at 340°, 350°, 360°, 10°, 20°, 30°, 40°, 50°, 60°, 70°, 80°, and then 90°, thereby creating a first 130° arc of treatment points on the superior side of the eye E. Thus, a series of individual applications with precisely defined angular spacing or radial displacements are made. A second 130° arc of treatment points on the inferior side of the eye E may then be created, starting from directing laser energy toward the point at 220° and then toward successively counter-clockwise points every 10° until a point at 100°.

Figure 6E:
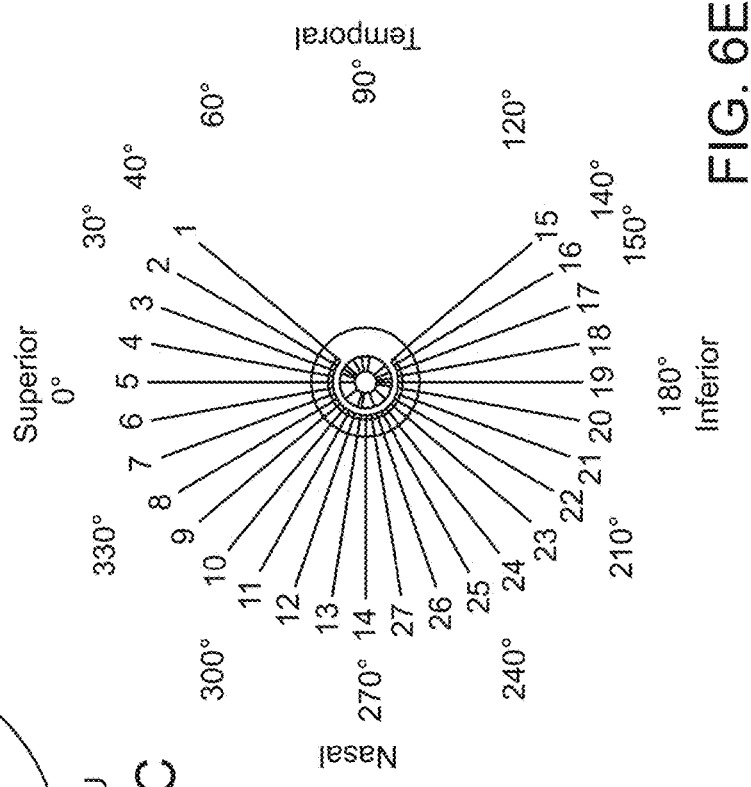
Figure 6D:
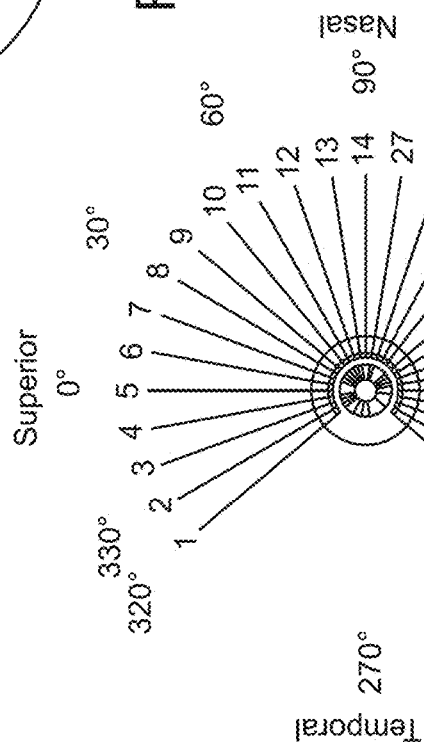

As shown in FIG. 6E, a similar procedure of directing laser energy toward a plurality of treatment points can be made on the left eye. Laser energy is directed toward a point at 40° and then successively counterclockwise until a point at 270°, creating a first 130° arc of treatment points. Then, laser energy can be directed toward a point at 140° and then successively clockwise every 10° until a point at 260°. In some embodiments, laser energy may be exposed to each point for about 1.0 seconds at a power of 1.5 W. The duty cycle of the laser energy may be 10%, with an "on" time of about 200 μs and an "off" time of about 1800 μs. The laser energy may be pulsed to avoid undesired thermal damage, for example, about 500 pulses may be delivered for each exposure of about 1.0 seconds. The eye E may also be treated at more or less treatment points at different areas, for example, the eye E may be treated so that a superior arc and an inferior arc of each of 150° or even 180° can be created. For example, 20 stationary applications over 360° may be made, with 5 stationary applications per quadrant. Treatment points may also be alternatively spaced apart from each other by other angles besides 10°, for example, by providing handpieces with different distances between edges 160. The pulsed laser systems and methods may comprise a Micro-Pulse™ Laser System and method.

In other embodiments, handpiece 110 may be slid or "painted" over a targeted region of the eye all the while laser energy is being emitted. For example, tip 115 may first be positioned about 3 mm posterior the limbus at the 10 o'clock or 300° position of the eye and gradually slid clockwise until the 2 o'clock or 60° position, all the while exposing the targeted region of the eye, e.g., the pars plana, with pulsed laser energy. Thus, if the width of surface 110 spans 30°, a superior treatment arc of 150° can be created. An inferior treatment arc of 150° can likewise be created by positioning tip 115 about 3 mm posterior the limbus at the 8 o'clock position or 240° and gradually sliding handpiece 110 until it reaches the 4 o'clock position or 120°, all the while exposing the targeted region of the eye, e.g., the pars plana, with pulsed laser energy. In exemplary embodiments, the duration of laser energy exposure for each treatment arc may be 50 seconds and the power of the laser may be 2 Watts. A total of 31,250 pulses at a rate of 625 pulses per second may be made during the 50 seconds. Each pulse may have an energy of 1.0 mJ. The size of the treatment arcs may vary. The treatment arcs, for example, may comprise a 180° superior arc and a 180° inferior arc.

EXPERIMENTAL SECTION

Experiment A

An initial study using a handpiece with a contact probe similar to those described above was conducted at the National University Hospital in Singapore. In the study, treatment procedures similar to those described above were conducted on a number of glaucomatous eyes. This initial study tracks glaucomatous eyes for about 6 months, the treated eyes being treated with the aforementioned handpiece and a treatment procedure using pulsed laser energy.

Patients with advanced glaucoma refractory to maximum tolerated medical and surgical treatment and a visual acuity of worse than 6/60 were included in the study. Patients with recent eye surgery within 3 months of enrollment, active ocular inflammation or inability to give informed consent were excluded.

The procedure was performed by a single surgeon to patients under local anesthesia. The contact probe was designed for accurate positioning of a fiber optic at 3.4 mm behind the limbus of the eye.

The laser settings were 2000 mW, applied over a total duration of 100 s, with a pulse duration of 0.6 s and a pulse interval of 1.1 s. Shots were applied over 360° avoiding the 3 o'clock and 9'oclock regions and any areas of thinning.

The main outcome measure was success of treatment, defined as a 30% or more reduction of IOP from baseline or an IOP of less than 21 mm Hg at 6 month follow-up.

23 eyes of 23 patients were treated. The patients had a mean age of 62.9±20.3 years. The mean duration of follow-up was 5.3±1.5 months. The mean pre-treatment IOP was 37.1±9.5 mm Hg.

TABLE 1 below summarizes mean IOP before and after treatment at 1 day, 1 week, 1 month, 3 months, and 6 months post-op. All mean post-treatment IOPs were significantly lower than the pre-treatment IOPs (paired Student's t-test, $p<0.001$).

TABLE 1

POST-OP IOP MEAUSREMENTS

| Time Point | Meant IOP (mm Hg) | Mean IOP Reduction (%) |
|---|---|---|
| Baseline | 37.1 ± 9.5 | — |
| 1 day post-op | 28.7 ± 10.8 | 24.0 ± 17.1 |
| 1 week post-op | 25.6 ± 9.8 | 30.9 ± 18.7 |
| 1 month post-op | 22.2 ± 7.0 | 38.2 ± 19.6 |
| 3 months post-op | 22.9 ± 8.9 | 35.4 ± 24.2 |
| 6 months post-op | 23.7 ± 9.7 | 37.6 ± 19.4 |

The rate of success of the treatment, defined as a 30% or more reduction from baseline or a final IOP of less than 21 mm Hg at the $6^{th}$ month follow-up visit. The success rate was 38% at 1 day, 57% at 1 week, 76% at 1 month, 80% at 3 months and 69% at 6 months. None of the patients had hypotony or loss in their best corrected visual acuity.

Experiment B

A similar study using a handpiece with a contact probe similar to those described above was conducted also at the National University Hospital in Singapore. In the study, treatment procedures using pulsed laser energy similar to those described above were conducted on a number of glaucomatous eyes. This study tracks the treated eyes for up to 18 months.

The MicroPulse™ procedure was performed by a single surgeon in the outpatient setting. Regional anesthesia with peribulbar or retrobulbar injection of 2% lidocaine was given prior to the procedure. Scleral transillumination was used to identify the position of the ciliary body as well as any areas of thinning. A diode laser emitting ball-lens tip contact probe, which is similar to those described above, was applied axially at the limbus. This probe housed a quartz fiberoptic of 600 μm in diameter. Its end protrudes 0.7 mm from the handpiece. The probe was specifically designed to allow positioning of the fiberoptic at 3.4 mm behind the surgical limbus, i.e., the distance from the reference edge of the contact surface of the probe to the fiberoptic was 3.4 mm. The laser settings were 2000 mW, over a total duration of 100 s, with a train of repetitive pulses each with a pulse duration of 0.5 ms and a pulse interval of 1.1 ms. The treatment was applied by "painting" or moving the probe continuously over 360 of the ciliary body, avoiding the 3 and 9 o'clock meridians and any area of thinned sclera. Total energy delivered to the ciliary body was 60-90 J.

The amount of intraoperative pain experienced by the patient was recorded and additional regional anesthesia was administered as required. Postoperatively, topical prednisolone acetate 1% was prescribed four times daily along with oral mefenamic acid for 5 days. Follow-up examinations were performed at 1 day, 1 week, 1 month, 3 months, 6 months, 12 months, and 18 months. Pain scoring, visual acuity, Goldman applanation tonometry, slit lamp biomicroscopy and dilated fundus examinations were carried out at every visit. Retreatment over 360 degrees was performed between 1 to 3 months if IOP reduction was less than 20%.

Statistical analysis was performed using SPSS software version 15.0. Means were compared using the two-tailed paired Student's t-test, with p<0.05 being considered significant.

46 eyes of 44 patients were evaluated in this study. The mean age of the patients was 63.2±16.0 years. There were 36 men (81.8%). Right eyes of 17 (38.6%) patients, left eyes of 23 (52.3%) patients and both eyes of 2 patients underwent MicroPulse™ treatment with TSCPC. TABLE 2 below shows the distribution of glaucoma diagnoses. Four eyes received retreatment between 1 to 3 months after the initial laser.

TABLE 2

DISTRIBUTION OF GLAUCOMA DIAGNOSES

| Type of Glaucoma | No. (%) |
|---|---|
| Neovascular glaucoma | 17 (38.6%) |
| Primary open angle glaucoma | 10 (22.7%) |
| Primary angle closure glaucoma | 10 (22.7%) |
| Others | 7 (16.0%) |

TABLE 3 below summarizes mean IOP before and after treatment at 1 day, 1 week, 1 month, 3 months, 6 months, 12 months, and 18 months post-op. All mean post-treatment IOPs were significantly lower than the pre-treatment IOPs (paired Student's t-test, p<0.001). The mean duration of follow-up was 16.2±4.5 months.

TABLE 3

POST-OP IOP MEAUSREMENTS

| Time Point | Mean IO (mm Hg) | Mean reduction in IOP from baseline (%) |
|---|---|---|
| Baseline | 39.1 ± 12.7 | — |
| 1 day | 31.1 ± 13.5 | 21.6 |
| 1 week | 28.1 ± 12.1 | 28.1 |
| 1 month | 27.6 ± 12.8 | 28.4 |
| 3 months | 27.2 ± 12.8 | 23.5 |
| 6 months | 26.0 ± 13.4 | 27.2 |
| 12 months | 26.5 ± 12.6 | 27.3 |
| 18 months | 26.9 ± 11.8 | 30.5 |

Figure 7:
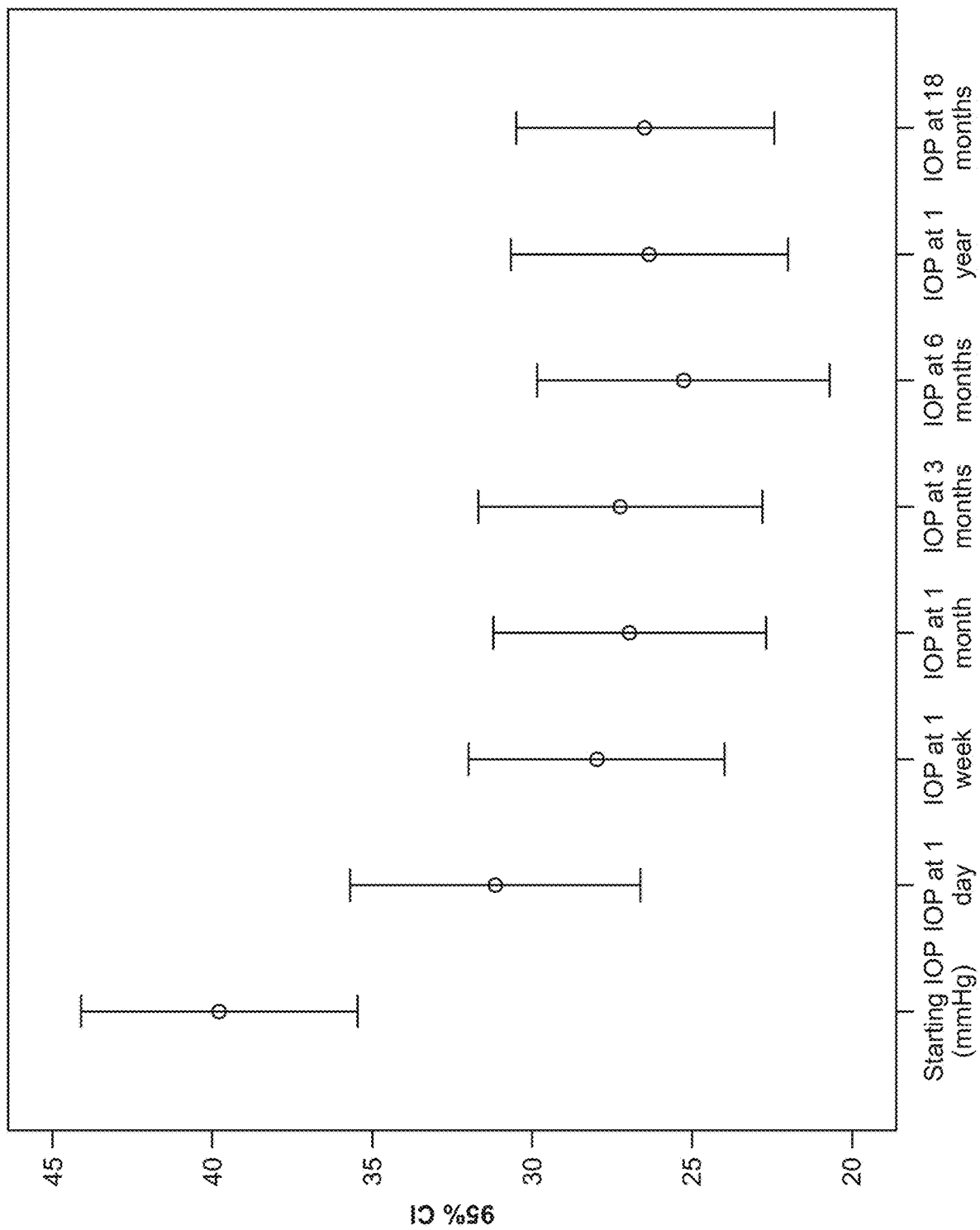
FIG. 7 shows a chart of exemplary experimental results of a conducted study using devices and methods according to embodiments of the present invention.

As shown in FIG. 7, the decrease in IOP appears to be gradual and sustained over 6 months. All patients who required systematic acetazolamide (n=6) prior to the treatment were able to discontinue the drug by the first postoperative day. The mean number of topical anti-glaucoma medication was reduced from 1.8±1.1 to 1.4±1.1 at 6 months follow up (p=0.003).

During the procedure, 15 patients (34.0%) reported some pain but found it to be tolerable and did not require additional anesthesia. Two patients (4.0%) required additional regional anesthesia. Post procedure, 7 patients (15.9%) reported mild pain on the first day. None required oral analgesia beyond the first day of treatment. All patients had mild postoperative inflammation at day 1 in the form of 1+ anterior chamber cells with slight conjunctival hyperemia. This inflammation resolved by 2 weeks post treatment in 40 patients (90.9). None of the patients experienced deterioration of their best-corrected visual acuity at final follow-up. One patient who had no light perception before the MicroPulse™ procedure underwent evisceration at 1 month for corneal perforation secondary to infection of a pre-existing bullous keratopathy. No patient developed hypotony, defined as an IOP of less than 5 mm Hg.

The IOP lowering efficacy of the studied method is comparable to conventional ciliary body photo-coagulation. The rapidity of IOP reduction, seen as early as 1-day post treatment, is an additional advantage over traditional laser treatment. The rapid reduction in IOP seen may be due to enhanced outflow facility from the uveal and suprachoroidal spaces as the novel probe targets the ciliary body epithelium of the pars plicata and/or the pars plana. Low laser pulses allow for repetitive series of sub-threshold intensity pulses of energy to be delivered with rest periods in between. "Painting" may also allow for a more even distribution of effect and a larger area to be treated compared to conventional laser treatment. A biological response may be triggered to lower IOP and yet excessive thermal damage to the ciliary epithelium and processes is avoided, as seen in histological specimens after conventional laser treatment. The limitation of adjacent tissue damage seen in the Micro-Pulse™ procedure may also explain the absence of complications such as hypotony.

It is to be understood that the above description is intended to be illustrative and not restrictive. Many embodiments will be apparent to those of skill in the art upon reviewing the above description. The scope of the invention should, therefore, be determined with reference to the appended claims, along with the full scope of equivalents to which such claims are entitled.

What is claimed is:

1. A laser treatment method for an eye, the eye having an optical axis, a pars plana posterior to a pars plicata and a pre-laser treatment intraocular pressure, the method comprising:
   positioning a probe in contact with an outer surface of a sclera of the eye so that a laser energy delivery tip of the probe is oriented transverse to the outer surface of the sclera toward the pars plana of the eye to define a treatment axis that is angularly offset from the optical axis of the eye;
   directing laser energy from the oriented laser energy delivery tip of the probe to the pars plana of the eye to a first application site in a target region; and
   repositioning the probe and directing laser energy to a plurality of additional application sites in the target region while maintaining an orientation of the probe at each application site so that the laser energy delivery tip is transverse to the outer surface of the sclera with the treatment axis angularly offset from the optical axis of the eye;
   wherein an aggregate amount of laser energy is sufficient to maintain a reduction from the pre-laser treatment intraocular pressure.

2. The method of claim 1, wherein the amount is sufficient to maintain the reduction from the pre-laser treatment intraocular pressure more than 5 months after the laser energy is delivered.

3. The method of claim 1, wherein the amount of laser energy is sufficient to increase uveoscleral outflow so as to maintain the reduction from the pre-treatment intraocular pressure.

4. The method of claim 1, wherein the amount is not sufficient to effect therapeutic photocoagulation.

5. The method of claim 1, wherein the treatment axis is generally perpendicular with the outer surface of the sclera of the eye.

6. The method of claim 1, wherein positioning the tip of the probe in contact with the outer surface of the eye comprises positioning a reference structure of a contact surface of the probe in alignment with a reference feature of the eye, the laser delivery tip being disposed along the contact surface so that the laser energy is delivered posteriorly to a limbus of the eye by over 2 mm.

7. The method of claim 6, wherein the reference feature of the eye comprises the limbus, and wherein the reference structure of the contact surface comprises a feature separated from the laser delivery tip by over 2 mm, wherein the feature extends between opposed lateral placement sides of the contact surface, and wherein the laser energy is delivered to the first pars plana region while the probe is held at a fixed position against the eye, and further wherein repositioning the probe at the additional application sites in the target region includes incrementally moving the probe laterally, with reference to of the contact surface, along the limbus so as to sequentially treat a plurality of circumferentially offset regions of the pars plana.

8. The method of claim 6, wherein the reference feature of the eye comprises the limbus, and further wherein repositioning the probe at the additional application sites in the target region includes moving the probe in a sliding motion along the limbus so as to treat an arc region using a superior sweeping stroke and an inferior sweeping stroke.

9. The method of claim 8, wherein the additional application sites are discrete with one another and with the first application site in the target region.

10. The method of claim 8, wherein the additional application sites are contiguous with one another and with the first application site in the target region.

11. The method of claim 1, further comprising maintaining an orientation of the probe so that the laser energy from the probe is directed with a transcleral orientation toward the pars plana, pars plana-pars plicata junction, or pars plicata of the eye.

12. The method of claim 1, wherein the laser energy comprises infrared laser energy and total laser energy directed to the pars plana is less than 75 J.

13. The method of claim 1, wherein the laser energy is delivered from a plurality of fixed probe locations, wherein the laser energy has a wavelength of 810 nm.

14. The method of claim 1, wherein the laser energy comprises pulsed laser energy or continuous wave emission mode.

15. The method of claim 14, wherein the laser energy comprises pulsed laser energy having a duty cycle of about 20% or less.

16. The method of claim 14, wherein the laser energy comprises pulsed laser energy delivered from a plurality of fixed probe locations, wherein each pulse has an energy of less than 2 mJ, and wherein the total laser energy directed to the pars plana is between about 40 J and 100 J.

17. A laser treatment method for treating an eye by reducing intraocular pressure, the method comprising:
   positioning a contact surface of a probe in contact with a surface of the eye, wherein the contact surface comprises an output aperture for delivering laser energy, and wherein the contact surface is positioned such that the output aperture is posterior to a limbus of the eye by a desired distance;
   performing a first sweep of the output aperture of the probe across the surface of the eye while the output aperture of the probe is maintained at the desired distance posterior to the limbus of the eye; and
   delivering laser energy toward a target region of the eye posterior to the limbus while the output aperture of the probe is swept across the eye and maintained in contact with the surface of the eye such that an aggregate amount of the laser energy reduces intraocular pressure of the eye.

18. The method of claim 17, wherein a treatment axis along which the laser energy is delivered is generally perpendicular to an outer surface of a sclera of the eye.

19. The method of claim 17, wherein a treatment axis along which the laser energy is delivered is angularly offset from an optical axis of the eye.

20. The method of claim 17, wherein a treatment axis along which the laser energy is delivered is substantially perpendicular to a line tangent to the contact surface at the output aperture.

21. The method of claim 17, wherein the first sweep comprises sliding the output aperture in a treatment arc range between 130 degrees and 180 degrees around the limbus of the eye.

22. The method of claim 17, wherein the first sweep is performed in a single continuous motion.

23. The method of claim 17, wherein the first sweep comprises a series of discrete spaced applications.

24. The method of claim 17, wherein performing the first sweep comprises continuously sliding the output aperture along a superior arc around the limbus of the eye in a first region of the eye.

25. The method of claim 24, further comprising performing a subsequent sweep of the output aperture, wherein the subsequent sweep comprises continuously sliding the output aperture along an inferior arc around the limbus of the eye in a second region of the eye, wherein the second region is distinct from the first region.

26. The method of claim 17, wherein sweeping the output aperture comprises continuously sliding the output aperture along a first arc around the limbus of the eye in a first region of the eye, the method further comprising:
performing one or more subsequent sweeps of the output aperture, wherein the one or more subsequent sweeps comprises continuously sliding the output aperture along one or more subsequent arcs around the limbus in one or more subsequent regions of the eye until the first sweep and the subsequent sweeps in combination define an annular pattern around the limbus.

27. The method of claim 17, further comprising repositioning the contact surface of the probe to another position posterior to the limbus of the eye by the desired distance and circumferentially offset from the target region about an optical axis of the eye; and
delivering laser energy toward a second region of the eye with the output aperture in contact with the surface of the eye while sweeping the probe across the eye in an arc motion.

28. The method of claim 27, further comprising selecting the desired distance based on a location of the target region.

29. The method of claim 17, wherein the target region comprises a pars plana of the eye, a pars plana-pars plicata junction, or a pars plicata of the eye.

30. The method of claim 17, wherein the laser energy comprises pulsed laser energy or continuous wave emission mode.

31. The method of claim 30, wherein the reference structure of the contact surface is at an edge of the contact surface that extends between opposed lateral placement sides of the contact surface, and wherein the first sweep comprises moving the probe in an arc around the limbus with reference to the reference structure.

32. The method of claim 17, wherein positioning the contact surface comprises positioning a reference structure of the contact surface in alignment with a reference feature of the eye such that the output aperture is posterior to the limbus of the eye by the desired distance.

33. The method of claim 17, wherein the laser energy is delivered from a plurality of fixed probe locations, and wherein the aggregate amount of the pulsed laser energy directed to the target region is between about 40 J and 100 J.

* * * * *